United States Patent [19]
Schneider et al.

[11] Patent Number: 4,818,705
[45] Date of Patent: Apr. 4, 1989

[54] METHOD AND APPARATUS FOR ANALYZING THE COMPOSITION OF THE EXHAUST GAS OF ANY INTERNAL COMBUSTION ENGINE

[75] Inventors: Gerd Schneider, Wegberg; Franz-Wilhelm Boost, Monchen-Gladbach; Frank Leimbach, Wuppertal, all of Fed. Rep. of Germany

[73] Assignee: Pierburg GmbH, Neuss, Fed. Rep. of Germany

[21] Appl. No.: 25,000

[22] Filed: Mar. 12, 1987

[30] Foreign Application Priority Data

Mar. 12, 1986 [DE] Fed. Rep. of Germany ....... 3608122

[51] Int. Cl.$^4$ ............................................. G01N 21/85
[52] U.S. Cl. ...................................... 436/164; 422/91; 422/98; 356/418; 356/435; 356/437
[58] Field of Search ............... 250/227; 356/435, 437, 356/418, 438; 422/91, 98; 436/164

[56] References Cited

U.S. PATENT DOCUMENTS

| | | | |
|---|---|---|---|
| 3,773,426 | 11/1973 | Mudd | 356/435 |
| 3,790,289 | 2/1974 | Schmidt | 356/438 |
| 3,796,887 | 3/1974 | Vincent et al. | 356/439 |
| 3,860,818 | 1/1975 | Stalder et al. | 356/437 X |
| 3,908,167 | 9/1975 | Hulls et al. | 356/438 |
| 4,164,373 | 8/1979 | Schuss et al. | 356/317 X |
| 4,420,687 | 12/1983 | Martinez et al. | 356/437 |
| 4,477,190 | 10/1984 | Liston et al. | 356/418 |
| 4,480,190 | 10/1984 | Burough et al. | 356/437 |
| 4,661,320 | 4/1987 | Ito et al. | 422/91 X |
| 4,692,621 | 9/1987 | Passaro et al. | 356/437 |

Primary Examiner—Barry S. Richman
Assistant Examiner—Timothy M. McMahon
Attorney, Agent, or Firm—Roberts, Spiecens & Cohen

[57] ABSTRACT

A device for analyzing the composition of the exhaust gas of an internal combustion engine in which a light source provides a light beam absorbable by the exhaust gas, and a plurality of measurement cells are traversed by radiation of the light beam while the exhaust gas flows through the cells. A corresponding number of radiation detectors are arranged after the measurement cells to receive the absorption attenuated light radiation and to produce an electrical measurement signal. At least one light interrupter periodically interrupts the light radiation. A particularly accurate analysis of the composition of the exhaust gas is obtained, even for dynamic operating conditions of the internal combustion engine, during every phase of the combustion cycle if the light interrupter is arranged directly behind the light source and the light radiation used for the measurement is periodically interrupted as a whole and if, furthermore, each of the measurement cells has a respective radiation filter associated therewith and with the radiation detectors and if a light dividing device is arranged between the light interrupter and the measurement cells for the simultaneous application of the light radiation on all measurement cells.

13 Claims, 1 Drawing Sheet

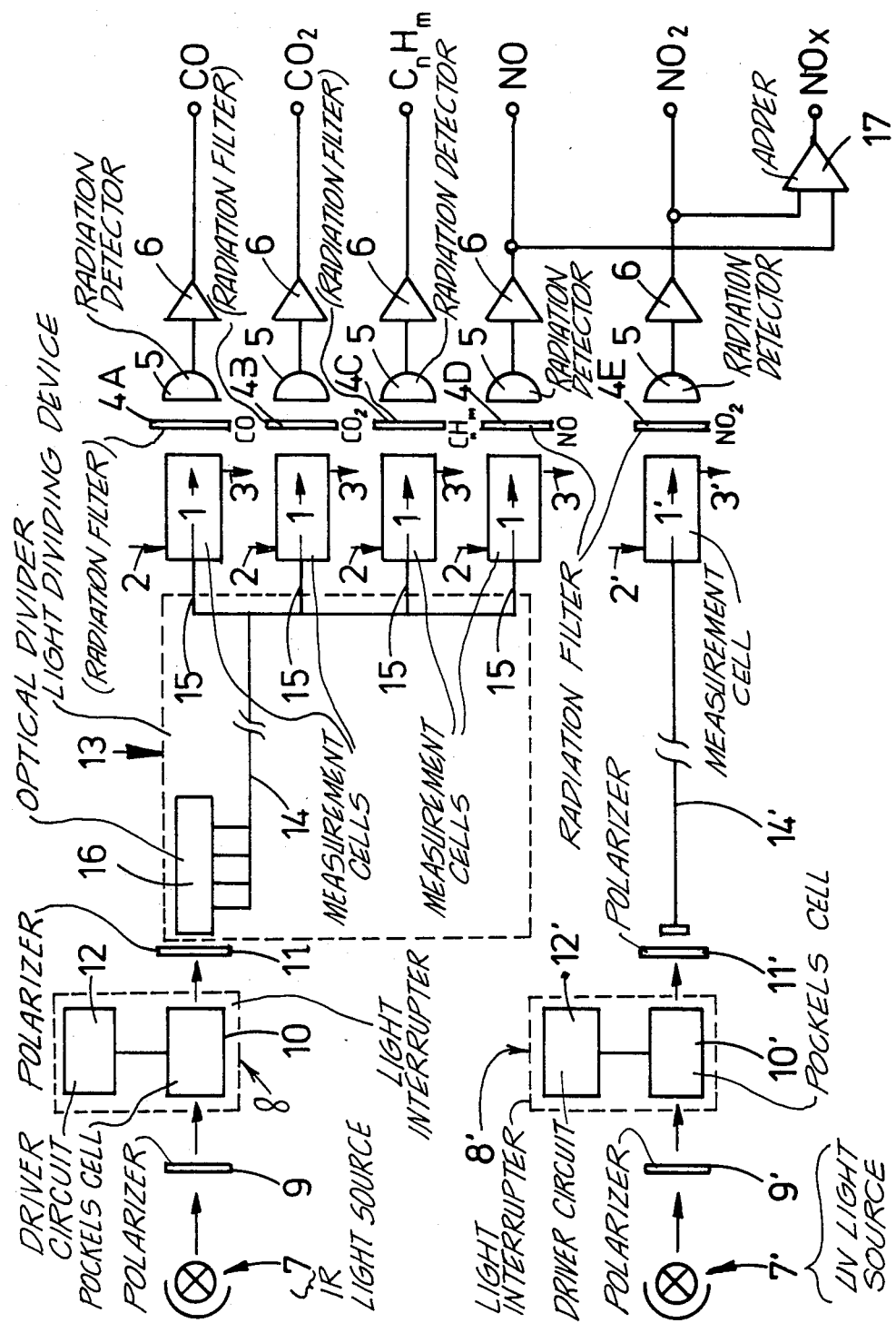

METHOD AND APPARATUS FOR ANALYZING THE COMPOSITION OF THE EXHAUST GAS OF ANY INTERNAL COMBUSTION ENGINE

FIELD OF THE INVENTION

The present invention relates to a measuring apparatus and method for analyzing the composition of the exhaust gas of an internal combustion engine, comprising:

1. a light source for a light beam which can be attenuated by being absorbed by the components of the exhaust gas to be analyzed,
2. a measurement cell through which the light beam passes and which is traversed by the exhaust gas,
3. a radiation detector arranged in the path of the light beam behind the measurement cell to receive the absorption-attenuated light radiation and produce an electrical measurement signal in response thereto,
4. a light interrupter for periodic interruption of the light radiation, and
5. radiation filters tuned to the gas components to be measured.

DESCRIPTION OF PRIOR ART

The known measuring apparatus serves for analyzing the concentration of at least two gas components and is available on the market, as a CO—$CO_2$ lambda tester. In the known measuring apparatus the collected, directed light of an IR radiator passes through a measurement cell traversed by the gas to be analyzed and at the output side of the measurement cell there is arranged a so-called chopper wheel and then a pyroelectric detector (solid-state detector) with preamplifier. The chopper wheel rotates precisely at a speed of rotation of about 50 Hz. The chopper wheel has rectangular slits which permit the light beam to pass periodically from the measurement cell to the detector whereas the solid rectangular material between the slits interrupts the light beam. In the slits are inserted interference filters and adjacent interference filters are transparent to difference narrowly limited wavelength ranges in the IR region corresponding to the absorption bands of the gas components whose concentration is to be measured in each case.

With this known measuring device, therefore several components of the gas flowing through the measurement cell can be measured with a single measuring arrangement consisting of a light source, a measurement cell and a detector. The disadvantages of this known measuring device are that the gas components to be measured are detected one after the other in time, a complete measurement cycle takes about 0.17 seconds, and the entire measuring device forms an inseparable one piece unit of relatively large size. Such a measuring device is therefore suitable only for integral analysis of the composition of the exhaust gas of internal combustion engines.

SUMMARY OF THE INVENTION

Proceeding from the above, an object of the invention is to provide a measuring method and device of this type which assures an exact analysis of the composition of the exhaust gas under dynamic operating conditions of internal combustion engines, such as change in gas composition in each phase of the combustion cycle.

This object is achieved in that:
the light interrupter is arranged directly behind the light source and periodically interrupts the light radiation, as a whole, used for the measurement;
for each gas component to be measured there is provided a separate measurement cell, a separate radiation filter for each measurement cell and a separate radiation detector, and all of the measurement cells are traversed simultaneously by the exhaust gas; and
a light-dividing device is arranged between the light interrupter and the measurement cells for the simultaneous application of the light radiation on all of the measurement cells.

The invention is based on the basic concept of providing a measuring device for the simultaneous analysis of a plurality of gas components of a flowing gas whereby a particularly accuratae determination of the concentrations of several gas components of a rapidly varying gas mixture is possible.

This provides the following advantages:
all gas components are measured precisely simultaneously;
only a single light source and a single light interrupter are necessary;
all measurement cells are traversed by light of identical characteristic values pulsed in the same phase;
measurement errors caused by the radiation filters are minimized since the radiation filters, arranged in front of the measurement cell but preferably downsteam in the ray path, do not move but are fixed in space;
the measurement device is suitable for the measurement of the composition of the exhaust gas directly downstream of the combustion chamber of an internal combustion engine and therefore for the measurement of relatively hot gases, since the measurement cells can be arranged relatively far from the very sensitive light interrupter, as a result of which, the dimensions of the measuring device can also be better adapted to the local conditions than was possible up to now; in this way the gas paths to the measurement cells, and thus the delay times between changes in composition of the gas mixture and the determination of this change in composition, are kept particularly short; consequently, the measuring device can also be used for concentration-dependent control actions in the case of rapid changes of concentration.

In one practical embodiment of the invention, the light dividing device consists of a fiber optical system in which one end of a bundle of light conducting fibers is optically coupled with the outlet of the light interrupter and the other end, which is divided into partial bundles, is optically coupled with the light inlets of the measurement cells. In this way, exactly identical light beams are assured between the light interrupter and the measurement cells, as well as a uniform distribution of intensity of the light over the measurement cells. Moreover, a flexible arrangement is possible. For the uniform distribution of the light over the cross section of the light bundles at the coupling locations a coupling or uncoupling optical system can be provided to assure the parallelism of the beams of light in the elements to be coupled optically and a complete and uniform illumination of the coupled cross sectional surfaces; in this way, therefore, the light conducting cross sections of the bundles of the light conducting fibers as well as the partial bundles formed therefrom, and also, however the entrance surfaces of the light inlets of the measurement cells, are completely and uniformly utilized and illuminated.

In accordance with a preferred embodiment of the invention, the light interrupter consists of a light-pervious cell of electrooptically active material (i.e. material which is optically active in an electrical field), which cell is arranged between polarizers, and electrodes are arranged parallel to it and transversely to the light beam in order to produce an electrical alternating field. Such light interrupters, for instance, in the form of a Kerr cell but preferably in the form of Pockels cell, make it possible, in combination with a corresponding source of alternating voltage, particularly in the form of a driver circuit, to interrupt and open the light ray path at a high and stable frequency with predetermined slopes of the flanks of the signals; the alternating voltage can, for instance, be obtained in the form of an on/off circuit of the voltage applied to the electrodes. With such a light interrupter, dynamic, high-frequency changes in concentration can be measured for the first time, especially with high accuracy.

The use of such a light interrupter in combination with a measuring device of this type has proven extremely advantageous also for measurement with individual cells, i.e. without the use of a light dividing device.

The measuring device in accordance with the invention is operated in that the light coming from the light source is conducted in succession through the light interrupter and the light dividing device and then, in parallel, through the measurement cells and radiation filters associated therewith, to the detectors, with the formation of measurement signals.

Suitable development of the inventive concept assures, in particular, a high degree of dependability in operation, flexibility in use and precision in measurement.

The aforementioned structural elements or process steps of the invention are not subject to any special exceptions as to size, shape, selection of material, technical concept or process conditions, so that the criteria of selection known in the corresponding field of use can be applied, without limitation.

BRIEF DESCRIPTION OF THE FIGURE OF THE DRAWING

In the sole FIGURE of the drawing, there is diagrammatically illustrated an embodiment of a measuring device according to the invention.

DETAILED DESCRIPTION OF A PREFERRED EMBODIMENT

For the measurement of the gas components CO, $CO_2$, $C_n H_m$, NO and $NO_2$, for example, in the exhaust gas of an internal combustion engine, five measurement cells 1,1' are arranged in parallel in a conduit means for a flow of the gas therethrough. The cells have respective inlets 2,2' for the entry of the gaseous mixture to be analyzed, and the inlets 2,2' are disposed precisely at the same longitudinal location in the flow path of the gaseous mixture. The gaseous mixture leaves the measurement cells 1 at gas outlets 3,3'. In the ray path downstream of the measurement cells 1,1' i.e., to the right of the measurement cells in the drawing, there are arranged radiation filters 4A to 4E which, in known manner, are constituted as bandpass filters to permit the passage only of the wavelength range characteristic of the radiation absorption of the gas component to be measured; in other words, in this embodiment, the gas components CO, $CO_2$, $C_n H_m$, NO and $NO_2$. Interference filters are preferred for this purpose. The radiation filters 4A to 4E have radiation detectors 5 thereafter and amplifiers 6 arranged behind the detectors. The radiation detectors are preferably ceramic pyroelectric detectors of known construction, for instance of lead zirconium titanate. They produce an electrical output signal which is a function of the received radiation flux.

For the uppermost four measurement cells in the drawing, only a single light source 7, for example, an infrared radiator is required. The light beam coming from the light source 7, passes, firstly through a light interrupter 8 which consists of a polarizer 9, a Pockels cell 10 and another polarizer 11 as well as a driver circuit 12. The polarizers 9 and 11 can be Nicols prisms. The Pockels cell consists, in known manner, of an electrooptically active material with electrodes arranged transverse to the light beam path and to which the driver circuit 12 applies high frequency alternating voltage. The frequency of the alternating voltage depends on the specific measurement to be made and the operating frequencies of the other components. When pyroelectric detectors are used, the frequency will be a maximum of 5 kHz as this is the maximum frequency which such detectors can resolve. For the resolution of periodically varying gas concentrations at least ten measurement cycles per period are recommended, so that at a frequency of 5 kHz, a differentiated analysis of the exhaust gas of internal combustion engines can be obtained for a speed of rotation of up to 30,000 rpm. In the Pockels cell 10 therefore the light path is interrupted and opened completely without inertia at high frequency in known manner, and the polarizers 9 and 11 block all undesired directions of oscillation of the light from the light source 7.

Coupled to the polarizer 11 is a light dividing device 13 constructed as a fiber optic assembly. The fiber optic assembly consists of a bundle of light conducting fibers 14 which are subdivided at the light outlet end into four equal partial bundles 15 which are optically coupled to the light inlets of the measurement cells 1. An uncoupling optical system, (not shown) can be interposed between the bundles 15 and the inlets of measurement cells 1. In the embodiment shown in the drawing, the light inlet of the fiber bundle 14 is provided with a so-called optical fiber divider 16.

For the measurement of the concentration of $NO_2$, a UV radiation source is preferably used since IR radiation is only slightly absorbed by $NO_2$. Therefore, a UV radiator is used as light source 7' while the other optical parts (except for the radiation filter 4E) can be the same as for IR radiation. The measurement value outputs for NO and $NO_2$ are preferably combined by an adder 17, to form an $NO_x$ measurement value output.

Although the invention has been described in relation to a specific embodiment thereof, it will become apparent to those skilled in the art that numerous modifications and variations can be made within the spirit and scope of the invention as defined in the attached claims.

What is claimed is:

1. A method of analyzing the composition of the exhaust gas of an internal combustion engine comprising:

providing a light beam from a light source which can be absorbed by the components in the exhaust gas to be measured, periodically interrupting the light beam, dividing the thus interrupted light beam into a plurality of parallel subdivided beams, directing the subdivided beams through respective measurement cells which are simultaneously traversed by the exhaust gas to be analyzed, filtering the output of the respective cells according to the components of the gas to be analyzed thereby, detecting the thus filtered light output and producing an electrical signal which is a function of the magnitude of said light output to provide indication of the magnitude of the components in the exhaust gas and thereby of the composition thereof.

2. A method as claimed in claim 1 further comprising combining two of said electrical signals to produce a further output value.

3. A method as claimed in claim 1 further comprising providing a second light source of different wavelength from the first said light source, periodically interrupting the beam from the second light source, directing the thus interrupted second beam through a further measurement cell which is traversed by the exhaust gas simultaneously with the first said measurement cells, filtering the beam which is output at the further measurement cell, detecting the thus filtered light output, producing an electrical signal which is a function of the magnitude of the light output and combining the latter electrical signal with one of the first said electrical signals.

4. A measuring apparatus for analyzing the composition of the exhaust gas of an internal combustion engine, said apparatus comprising:

a light source for producing a light beam which can be absorbed by components in an exhaust gas which are to be measured, a plurality of measurement cells each for a respective gas component of the exhaust gas which is to be measured, conduit means for passage therethrough of the exhaust gas and of light from the light source, means supporting said cells in said conduit means for simultaneous passage of the exhaust gas and light therethrough, a plurality of radiation filters one for each cell tuned to the gas component to be measured, a plurality of radiation detectors each arranged opposite each respective measurement cell, said filters being disposed between the measurement cells and the respective detectors such that the detectors each receive, via the respective filter, absorption attenuated light radiation to procude an electrical measurement signal as a function thereof, light interrupter means for the periodic interruption of the light beam from the light source, said light interrupter means being arranged in the path of the light beam between said light source and said measurement cells for periodically interrupting said light beam, and, light dividing means between the light interrupter means and measurement cells for dividing the interrupted light beam produced by said light interrupter means and simultaneously applying the thus divided interrupted light beam to all of the measurement cells.

5. A measuring apparatus as claimed in claim 4 wherein said radiation filters are band pass filters.

6. A measuring apparatus as claimed in claim 4 comprising a second light source for producing a light beam, and arranged in sequence therein, a second light interrupter means, a further measurement cell, a further radiation filter, a further radiation detector and means for combining the output of said further radiation detector with the output of one of the first said radiation detectors.

7. A measuring apparatus as claimed in claim 4 wherein said filters each are associated with stationary support means.

8. A measuring apparatus as claimed in claim 4, wherein said light interrupter means has an input for light from said light source and an outlet for periodic interrupted light, said light dividing means comprises a fiber optical system including a bundle of light conducting fibers having one end optically coupled to the light interrupter means at the outlet thereof and the other end divided into a plurality of partial bundles respectively optically connected to said measurement cells.

9. A measuring apparatus as claimed in claim 8 comprising means in said fiber optical system for selective coupling and uncoupling therewith to assure parallelism and light uniformity of said divided light beams.

10. A measuring apparatus as claimed in claim 8 wherein said light dividing means comprises an optical fiber divider.

11. A measuring apparatus as claimed in claim 4 wherein said light interrupter means comprises a light pervious cell of electrooptically active material, a pair of polarizers on opposite sides of said cell and means associated with said cell for impressing an electrical alternating field thereon.

12. A measuring apparatus as claimed in claim 11 wherein said light pervious cell is a Pockels cell.

13. A measuring apparatus as claimed in claim 12 wherein said means producing an electrical alternating field comprises a driver circuit coupled to said cell.

* * * * *